(12) United States Patent
List et al.

(10) Patent No.: US 8,888,715 B2
(45) Date of Patent: Nov. 18, 2014

(54) ANALYSIS SYSTEM AND METHOD FOR DETERMINING AN ANALYTE IN A BODY FLUID WITH A MAGAZINE COMPRISING INTEGRATED SAMPLE ACQUISITION AND ANALYZING ELEMENTS

(75) Inventors: Hans List, Hesseneck-Kailbach (DE); Stephan-Michael Frey, Griesheim (DE); Kai Fluegge, Aachen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 987 days.

(21) Appl. No.: 12/712,236

(22) Filed: Feb. 25, 2010

(65) Prior Publication Data

US 2011/0060246 A1 Mar. 10, 2011

Related U.S. Application Data

(63) Continuation of application No. PCT/CT2008/006456, filed on Aug. 6, 2008.

(30) Foreign Application Priority Data

Aug. 31, 2007 (EP) .................................. 07017058

(51) Int. Cl.
*A61B 5/00* (2006.01)
*B65D 81/00* (2006.01)
*A61B 5/15* (2006.01)
*A61B 5/151* (2006.01)

(52) U.S. Cl.
CPC ........... *A61B 5/1405* (2013.01); *A61B 5/15146* (2013.01)
USPC .......................................... 600/583; 600/584

(58) Field of Classification Search
USPC ................... 600/573, 583, 584; 606/181–183
See application file for complete search history.

(56) References Cited

U.S. PATENT DOCUMENTS

| 6,607,658 | B1 | 8/2003 | Heller et al. |
| 6,905,244 | B2 | 6/2005 | Kilcher et al. |
| 7,169,117 | B2 * | 1/2007 | Allen ............................ 600/584 |
| 2002/0052618 | A1 | 5/2002 | Haar et al. |
| 2003/0143113 | A2 | 7/2003 | Yuzhakov et al. |
| 2003/0212345 | A1 | 11/2003 | McAllister et al. |
| 2004/0034318 | A1 | 2/2004 | Fritz et al. |

(Continued)

FOREIGN PATENT DOCUMENTS

| WO | 2005018711 A2 | 3/2005 |
| WO | WO 2005/104949 A1 | 11/2005 |

(Continued)

*Primary Examiner* — Adam Eiseman
(74) *Attorney, Agent, or Firm* — Roche Diagnostics Operations, Inc.

(57) ABSTRACT

Analysis system for determining an analyte in a body fluid is presented. The system comprises a reusable analysis instrument and a magazine having a plurality of integrated sample acquisition and analyzing elements. Each element comprises a puncturing element and an analyzing element. A coupling unit couples the integrated sample acquisition and analyzing element to a drive. The magazine comprises a housing having a plurality of elongate neighboring chambers separated by two side walls running in a longitudinal. The chambers contain the integrated sample acquisition and analyzing element. The chambers have an exit opening allowing for the at least partial exiting of the puncturing element. The chambers of the magazine are accessible to a coupling element that can be formfitting coupled to the coupling structure of the puncturing element, when the puncturing element is in the chamber of the magazine and the magazine is located in a holder.

20 Claims, 6 Drawing Sheets

(56) References Cited

U.S. PATENT DOCUMENTS

| | | |
|---|---|---|
| 2004/0092995 A1 | 5/2004 | Boecker et al. |
| 2006/0008389 A1 | 1/2006 | Sacherer et al. |
| 2006/0200045 A1* | 9/2006 | Roe .............................. 600/583 |
| 2006/0229532 A1 | 10/2006 | Wong et al. |
| 2007/0149897 A1 | 6/2007 | Ghesquiere et al. |
| 2010/0036282 A1 | 2/2010 | List et al. |

FOREIGN PATENT DOCUMENTS

| | | |
|---|---|---|
| WO | WO 2006/031920 A2 | 3/2006 |
| WO | 2006038044 A2 | 4/2006 |
| WO | 2006092281 A2 | 9/2006 |

* cited by examiner

ANALYSIS SYSTEM AND METHOD FOR DETERMINING AN ANALYTE IN A BODY FLUID WITH A MAGAZINE COMPRISING INTEGRATED SAMPLE ACQUISITION AND ANALYZING ELEMENTS

CROSS-REFERENCE TO RELATED APPLICATIONS

This application is a continuation of PCT/EP2008/006456, filed Aug. 6, 2008, which is based on and claims priority to EP 07017058.4, filed Aug. 31, 2007, which is hereby incorporated by reference.

BACKGROUND

The present disclosure generally relates to an analysis system and method for determining an analyte in a body fluid and, in particular, to relates analysis system and method for determining an analyte in a body fluid comprising a reusable analysis instrument and a magazine having a plurality of integrated sample acquisition and analyzing elements.

To determine an analyte in a body fluid for diagnostic purposes, typically, small quantities of the fluid are taken from a body part. Frequently, blood is analyzed as a body fluid for this purpose. Puncturing devices having a lancet are used for the purpose of generating a wound in a body part, such as, for example, the fingertip or the earlobe. Puncturing devices of this type are implemented in such a manner that they can be used not only by medical personnel, but also by medical laypersons.

In general, a plurality of steps must be performed to determine an analyte in the body fluid. Firstly, a wound must be generated in the body part, from which a body fluid can exit. The body fluid is analyzed using a measuring unit. Typically, this can be performed using two devices operating independently from one another. The use of two devices is quite uncomfortable for the user. Therefore, combined systems are frequently used, which both generate the wound as well as analyze the exiting fluid.

In addition, to simple operation and increased operating comfort, a compact design of the devices can be important. In addition, piercing which is as pain-free as possible is a goal. This increases the acceptance of devices of this type for diabetics in particular, who have to determine the glucose content in their blood a plurality of times a day.

An integrated analysis instrument having a test sensor and a lancet is known, for example, from WO 2006/092281, which determines an analyte in a body fluid by electrochemical measurement. A capillary channel is provided in a test strip, via which a received body fluid is transferred to test electrodes, to determine an analyte by means of a measuring unit. The lancet is located on the bottom side of the test strip. The lancet is movable in relation to the test strip and is enclosed by a sterile envelope, from which it exits before piercing into the body part. The body fluid exiting from the wound is suctioned in by the capillary channel on the top side of the test strip and conducted to the electrodes of the electrochemical measuring unit. Because of the coupling mechanism of the analysis instrument to the integrated test sensor, the instrument is used with individual test sensors. Locating a plurality of disposable test sensors in a magazine is not provided.

To avoid complex use of individual integrated puncture and analyzing elements, analysis systems are known in which the puncture and analysis elements are stored in a magazine. Such a system is described, for example, in US 2003/0212345. The puncture and analyzing element used comprises a needle having a capillary channel, which is molded onto an analyzing element. Blood acquired during piercing is conducted through the capillary channel to the test zone of the puncture and analyzing element, which is implemented in one piece. The used elements are stored in a separate magazine or ejected from the system after use.

A plurality of systems are known in the prior art, in which integrated sensors having a puncturing element and an analyzing element are located in a magazine. U.S. Pat. No. 6,607,658, EP 1402818, and US 2002/0052618 disclose sensors of this type, for example. However, the sensors have to be completely removed from the magazine to be able to perform their function. This requires a relatively large construction of the analysis instruments.

An analysis system having an integrated puncture and analyzing element which is stored in a magazine is disclosed in US 2003/0143113. The puncture and analyzing element is not completely removed from the magazine, which simplifies the automated handling in the analysis system, in particular if the puncture and analysis system is moved back in the magazine after use. Because the puncture and analyzing element is implemented in one piece, the test zone of the analyzing element is also subjected to a sterilization of the puncturing element, so that the analysis capability of the test zone is reduced.

Therefore, there is a need for a compact analysis system in which a plurality of integrated sample acquisition and analyzing elements are stored.

SUMMARY

According to the present disclosure, an analysis system for determining an analyte in a body fluid comprising a reusable analysis instrument having a drive and a measuring and evaluation unit for measuring a measurement variable characteristic for the determination of an analyte and a magazine having a plurality of flat, disposable, integrated sample acquisition and analyzing elements, which each include a puncturing element and an analyzing element and have two major sides is presented.

In accordance with one embodiment of the present disclosure, the magazine comprises a plurality of flat, elongate, disposable, integrated sample acquisition and analyzing elements as well as the integrated sample acquisition and analyzing element itself, which comprises an analyzing element and a puncturing element having a tip. The puncturing element is movable on a movement path of a puncture movement in the puncturing direction and in relation to the analyzing element.

In accordance with another embodiment of the present disclosure, a method for generating a wound in a body part for analyzing a body fluid exiting from the wound by means of an analysis system is presented.

Accordingly, it is a feature of the embodiments of the present disclosure to a compact analysis system and method for determining an analyte in a body fluid comprising a reusable analysis instrument and a magazine having a plurality of integrated sample acquisition and analyzing elements. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
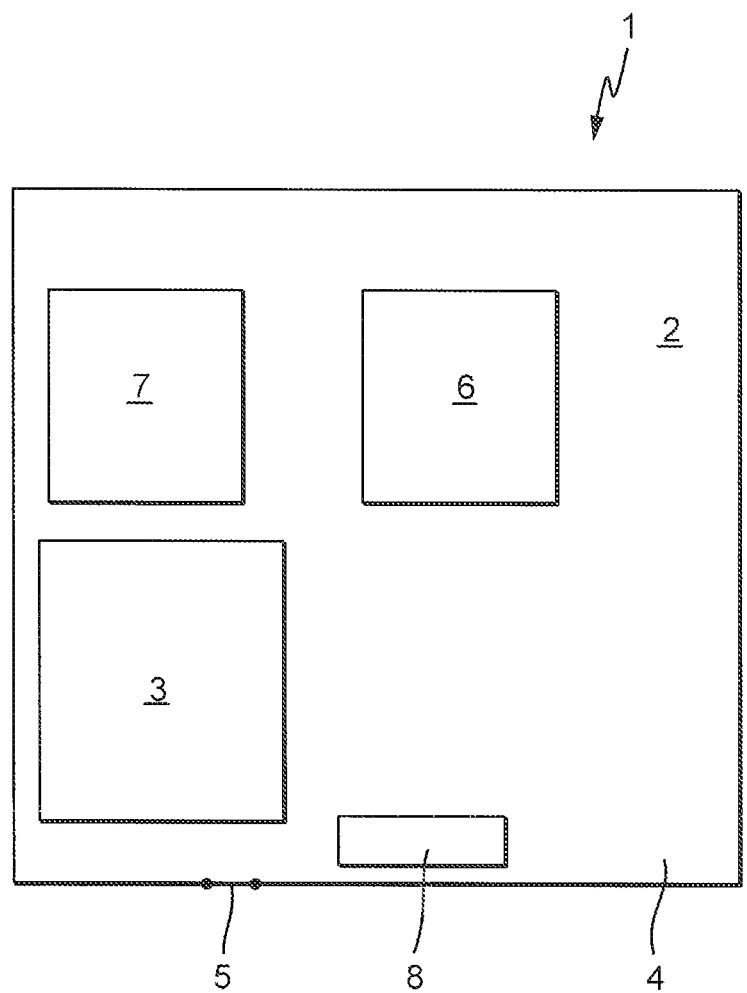
FIG. 1 illustrates a schematic illustration of the analysis system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The analysis system for determining an analyte in a body fluid can comprise a reusable analysis instrument and a magazine having a plurality of flat, disposable, integrated sample acquisition and analyzing elements, wherein each element can include a puncturing element and an analyzing element and can have two major surfaces. These integrated sample acquisition and analyzing elements are referred to in the art as "disposables". The terms, "disposables" or "dispos," also refer to the integrated sample acquisition and analyzing elements in the present disclosure.

The analysis instrument can have a drive for driving the puncture movement of the puncturing element, a coupling unit for coupling a disposable to the drive, and a measuring and evaluation unit for measuring a measurement variable, such as, for example, the determination of an analyte and the derivation of a desired analysis result. The analysis instrument can include a holder for holding the magazine. The magazine can comprise a housing having a plurality of neighboring elongate chambers separated by two side walls running in the longitudinal direction of the chambers. The height and length of the side walls can be greater than its width. The width can be defined by the distance of two neighboring side walls to one another. The chambers can have major sides delimited by the side walls and two long and two short minor sides extending between the side walls. One chamber can accommodate one disposable. Each chamber can have an outlet opening on one of its minor sides, through which a puncturing element of the disposable can move along the movement path and in the puncturing direction, can exit at least partially from the chamber.

The coupling unit of the analysis instrument can have a coupling element. The puncturing element can have a coupling structure which corresponds to the coupling element. The chambers of the magazine can be accessible for the coupling element of the coupling unit on one of their long minor sides in such a manner that the coupling element can be formfitting coupled to the coupling structure of the puncturing element when the puncturing element is positioned in the chamber of the magazine and the magazine is located in the holder of the analysis instrument.

The analysis system can be the compact construction allowing a close configuration of the individual disposables to one another. Two neighboring disposables can only be separated by a side wall between two chambers. In addition, the analysis system can offer simple access to the disposable, in particular to the puncturing element, to drive it on its movement path during the puncture movement.

The accommodation of the individual disposables in one chamber each can allow individual storage of the disposables. Therefore, not only the unused, new disposable can be stored in the magazine but also the disposable can also be returned back into the chamber after its use. Contamination of the still unused neighboring disposables in the magazine is precluded by the individual storage.

The magazine can be insertable into the holder of the analysis instrument. In one exemplary embodiment, a magazine of this type can comprise between about 10 and 50 disposables. In one embodiment, the magazine can comprise especially about 25 disposables. The content of the magazine can be sufficient for a user for several days. The user does not have to insert a new disposable into the analysis system after each puncture and analysis procedure. A new disposable can automatically be available before each puncture procedure.

The magazine can have the advantage that due to the edgewise positioning of the disposables, the individual parts can be stacked densely, so that space-saving storage of the disposables can be possible. Nonetheless, the disposables can be removed individually from the magazine because the coupling for their activation can be performed from the long minor side. The flat positioning of the disposables, one above the other, can lead to the advantage of a space-saving storage and an individual.

To further reduce the danger of contamination of a still unused disposable by an already used disposable, the major sides of the individual chambers delimited by the side walls can be closed. The minor sides of the chambers can also be at least partially closed. In one embodiment, all sides of the chambers can be closed. The long minor side, on which the chamber can be accessible for the coupling element of the coupling unit, and the short minor side, on which the exit opening can be located, can be covered by a film. The unused disposables can therefore be enclosed completely and hermetically sealed in a chamber of the magazine, precluding the risk of a contamination. The disposables can be kept dry easily. In one embodiment, a test field zone can be provided on the analyzing element which can have reagents used for determining the analyte can also be kept dry reliably and effectively.

The film for covering the chambers of the magazine can be, for example, a thin layer, a coating or a sheet of plastic, a foil or any other suitable material. The film can be adapted to be opened by or slit from the puncturing element and/or a coupling element of the coupling unit and/or another component of the analysis instrument. The film for covering the long minor sides of the chambers can typically be a one-piece film. The film can cover the magazine completely on the side on which the long minor sides of the chambers, through which the chambers can be accessible, can be located. This side of the magazine can be the top side. In one embodiment, the film can be attached to the front faces of the side walls forming the major sides by glue.

Additionally or alternatively, the exit openings of the chambers can also be covered by a film. In one exemplary embodiment, the film can be one piece and can extend over the entire side of the magazine on which the exit openings of the chambers can be located. The film can be glued or welded onto the front sides of the side walls.

In one embodiment, the film for covering the minor sides of the chambers can be at least partially metallic. The metal can be, for example, aluminum or an aluminum alloy. The film can also comprise a metallically coated or metallically vapor-deposited plastic. Metal films can have the advantage of being easy to pierce and separate. Uncontrolled further tearing of the film can be avoided. The seal of the neighboring chambers is not destroyed.

In another embodiment, the magazine can have a plurality of disposables, each comprising a puncturing element and an analysing element. The magazine can comprise a plurality of neighbouring chambers. Each chamber can contain a disposable. The puncturing element of the disposable can be enclosed by a protective envelope. Thereby, the puncturing element cannot get into contact with the analysing element of the disposable or a reagent complement of the analysing element.

In addition, the chambers can be covered with a film (on at least one of their sides), such that the chambers can be completely closed. The chambers can be enveloped so that they are hermetically sealed against the environment. Therefore, the disposable, especially the analysing element of the disposable, can easily be kept dry in the chamber such that no humidity or fluid can reach the inside of the chambers. The magazine can also be insertable into the holder of the analysis system according to the invention. The chambers of the magazine can have the same or an equal geometry as the chambers of the first magazine described.

In an exemplary embodiment of the magazine, the chambers can be accessible on one of their long minor sides, such that a coupling element of a coupling unit can be coupled to the disposable. At least the long minor sides, on which the chambers can be accessible, can be covered with a film.

In an exemplary embodiment, the disposable, which is stored in the and used in the analysis system, can have a test field zone. A body fluid to be analyzed can be placed on this test field zone. The body fluid can typically be blood, which will be described as an example in the following without restriction of the generality. The analyte to be determined can usually be glucose in the case of blood transfer. However, other components of the blood and/or the body fluid can be analyzed, such as lactates or similar substances known in the art.

The puncturing element of the disposable preferably can have a capillary channel having at least one sample inlet and one sample outlet. The movement path of the puncturing element can comprise a transfer position, in which the puncturing element can be positioned in relation to the analyzing element in such a position that the sample outlet of the capillary channel neighbors the test field zone of the analyzing element. The sample outlet can be located in relation to the test field zone in such a manner that a transfer of a body fluid from the capillary channel onto the test field zone can take place. A disposable of this type having a puncturing element having a capillary channel is described in greater detail in EP 07005222.0; its content is incorporated by reference.

The integrated sample acquisition and analyzing element (i.e., disposable) can have two major sides which can be diametrically opposite flat sides. The disposable can comprise an analyzing element and a puncturing element having a tip. The puncturing element can be movable on the movement path of a puncture movement in the puncturing direction and in relation to the analyzing element at the same time. The puncturing element can be enclosed by a protective envelope that can be comprised of plastic or a thin plastic film. The protective envelope can be connected to the puncturing element and the analyzing element. Upon a relative movement of the puncturing element to the analyzing element in the puncturing direction, the protective envelope can be telescoped. The tip of the puncturing element can penetrate the protective envelope and can extend out of the protective envelope.

The protective envelope can be connected to the rear end of the puncturing element in the puncturing direction (i.e., the end diametrically opposite the tip) by, for example, glue. The tip of the puncturing element can be mounted loosely in the protective envelope. This can ensure that the tip does not unintentionally destroy the protective envelope. The front area of the protective envelope, which is near the tip of the puncturing element, can connected by, for example, glue to the analyzing element.

The protective envelope of the disposable does not have to be opened or slit from a component of the analysis instrument. The forces to be applied by the component of the analysis instrument can be less in this type of disposable. The analysis instrument can therefore be implemented more simply, which results in lower production costs.

In one embodiment, the disposable can have a puncturing element which can have a coupling structure. A coupling unit of an analysis instrument can be coupled to the coupling structure to move the puncturing element on its movement path. The coupling element can correspond to the coupling structure of the puncturing element in such a manner that a formfitting coupling can be produced between the coupling element and the coupling structure. The coupling structure of the puncturing element can be located on a minor side or at the edge or edge side of the puncturing element, such that the coupling element can couple to the puncturing element from a direction traverse to the puncturing direction. The coupling movement can be in the same plane as the puncturing element.

In one embodiment, the puncturing element can comprise a needle element and an engagement element. The engagement element, which may also be called a retention element or carrier, can include the coupling structure of the puncturing element. The carrier can be coupled, or connected, to the needle element. For example, the carrier can be glued externally onto the protective envelope. The element and/or elements which can move during puncturing and can execute a puncturing movement on a movement path can be considered the puncturing element. The puncturing element can therefore also comprise further elements, for example, the carrier.

To generate a wound in a fingertip for analyzing blood exiting from the wound, a method having a plurality of steps can be executed according to the present invention. The method can be performed by an analysis system having at least a reusable analysis instrument and a magazine having a plurality of flat disposables. The disposables each can include a puncturing element and an analyzing element. The analysis instrument can have a drive and a coupling unit having a coupling element for coupling the analyzing element of the disposable to the drive. A measuring and evaluation unit and a holder for receiving the magazine can also be components of the analysis instrument.

The magazine can have a plurality of elongated neighboring chambers which each can receive one disposable. The chambers can be arranged in one rigid body, positioned parallel to each other in form of a linear array, or in form of a drum with the chambers alongside the cylindrical outer surface, or can be arranged radially, or semi radially, in a disc shaped body, or can be single chambers, movably connected to form a belt or a chain. The most compact arrangement can be a linear array.

The analyzing element of the disposable can have a test field zone in which the reagents for determining the analyte can be contained and a coupling structure. The chambers of the magazine in which the disposable can be stored can be accessible in such a manner that the coupling element of the coupling unit can formfitting couple to the analyzing element.

The method can comprise at least, coupling the coupling element of the coupling unit in a formfitting way to the coupling structure of the analyzing element. Subsequently, the analyzing element can be moved in the puncturing direction into an operational position, in which the analyzing element can extend from the chamber of the magazine so that the test field zone of the analyzing element can be positioned outside the magazine. A measurement variable characteristic for the determination of the analyte can be measured on the test field zone.

To measure the measurement variable, the test field zone can be located in the operational position outside the magazine. An optical measurement of the measurement variable can be performed. An electrochemical measurement can also be possible. The measurement optic can be located directly in front of the magazine. At least a part of the disposable can be located in the chamber of the magazine, so that the chamber can be used as a guide and holder for the disposable. Because the disposable can be guided by the chamber during its movement into the operational position. As it remains in this position, the mechanism of the analysis instrument for moving the disposable can be simpler than in systems in which the disposable is moved completely out of the magazine.

In one embodiment, the coupling unit can have a second coupling element and the puncturing element can also have a coupling structure. Further, the puncturing element can comprise a capillary channel having at least one sample inlet and one sample outlet. The capillary channel can be located on a needle element of the puncturing element. The coupling structure can be provided on the needle element itself or on a carrier connected to the needle element of the puncturing element, as described above.

The second coupling element can be formfitting coupled to the coupling structure of the puncturing element. The puncturing element can be moved in relation to the analyzing element on the movement path in the puncturing direction in such a position that the tip of the puncturing element can project beyond the analyzing element in the puncturing direction. A wound can be generated in a body part located in the puncturing direction in front of the analyzing element and a body fluid from the wound can be received to the sample inlet in the capillary channel of the puncturing element. This step can be performed when the analyzing element is already located in the operational position. Furthermore, the puncturing element can move relative to the analyzing S element into a transfer position in such a manner that the sample outlet of the capillary channel of the puncturing element can neighbor the test field zone of the analyzing element. The puncturing element and the analyzing element do not come into contact before the next step can be performed. The puncturing element and the analyzing element can contact one another, a contact pressure unit of the analysis instrument can pressing the sample outlet of the capillary channel against the test field zone.

Referring initially to FIG. 1, FIG. 1 schematically shows an analysis system 1. The analysis system 1 can comprise an analysis instrument 2, into which a magazine 3 can be inserted. The analysis instrument 2 can have a housing 4 having a housing opening 5 through which a disposable 15, or puncturing element stored in the magazine 3, can exit from the housing 4. The analysis instrument 2 can comprise a drive 6, a coupling unit 7, and a measuring and evaluation unit 8. The analysis instrument 2 can also include further components (not shown), such as, for example, a holder for the magazine 3.

Figure 2A:
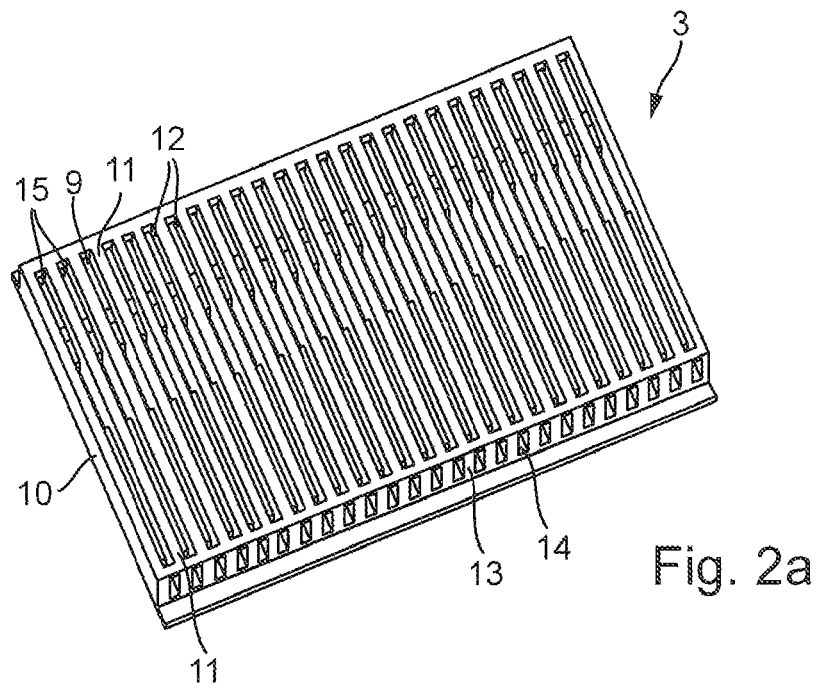
FIGS. 2a-b illustrate a magazine having a plurality of chambers according to an embodiment of the present disclosure.

The magazine 3 is shown in detail in FIGS. 2a and b. The magazine 3 can have a housing 3a having a plurality of neighboring chambers 9. The chambers 9 can be elongate slots or grooves. A side wall 10 running in the longitudinal direction, which can separate two chambers 9 from one another, can be located between each two neighboring chambers 9. The height and length of the side walls 10 can be greater than the distance between them. In this way, narrow, elongate chambers 9 can be formed having two major sides 11 delimited by the side walls 10 and two long minor sides 12 and two short minor sides 13 extending between the major sides 11.

As it can be seen from FIG. 2a, the chambers 9 can be open on their long minor side 12, which is directed upward in the figure. The short minor sides 13 visible in FIG. 2a can have an exit opening 14, through which a disposable 15 located in a chamber 9 can exit. The long minor sides 12 and the side walls 10 and major sides 11 can thus extend in the puncturing direction.

Figure 2B:
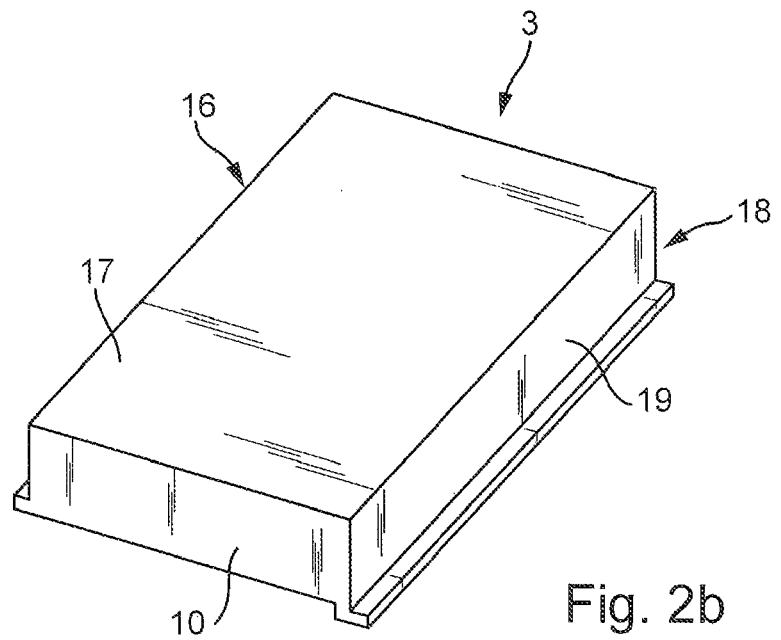
Figure 3A:
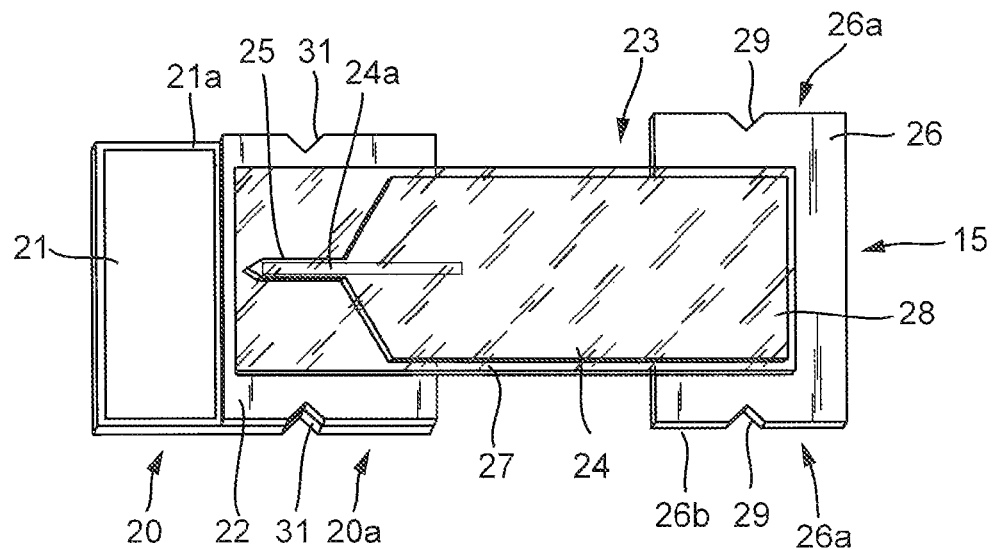
FIGS. 3a-b illustrate a detail view of the integrated sample acquisition and analyzing element according to an embodiment of the present disclosure.

FIG. 2b shows the magazine 3 from FIG. 3a, in which the top side 16 can be covered by a protective film 17. The protective film 17 can close the upwardly directed long minor sides 12 of the chambers 9. In one embodiment, the protective film 17 can be glued or welded onto the narrow, upwardly directed front sides of the side walls 10.

The short minor sides 13 of the chambers 9, which can have an exit opening 14 here, can be located on a front side 18 of the magazine 3. The front side 18 can be covered by a protective film 19 (like the top side 16). The protective film 19 can be glued or welded to the short front sides of the side walls 10. During the puncturing or analysis procedure, the disposable 15 can pass at least partially through the exit opening 14 penetrating the film 19. Alternatively, the protective film 17 and the protective film 19 can be formed by a single film. The protective films 17 and 19 can allow the individual chambers 9 of the magazine 3 to be completely enclosed and hermetically sealed. A disposable 15 located in one chamber 9 can thus be encapsulated relative to the environment. This can keep the disposables dry. The protective films 17, 19 can be films impermeable to water vapor, so that the unused disposable 15 in a chamber 9 can be kept dry. For this purpose a desiccant (i.e., a drying agent) can additionally be placed in the chamber 9. In one embodiment, the disposable 15 can comprise the desiccant (e.g., in form of a carrier). A further desiccant then does not have to be placed in the chamber.

Figure 3B:
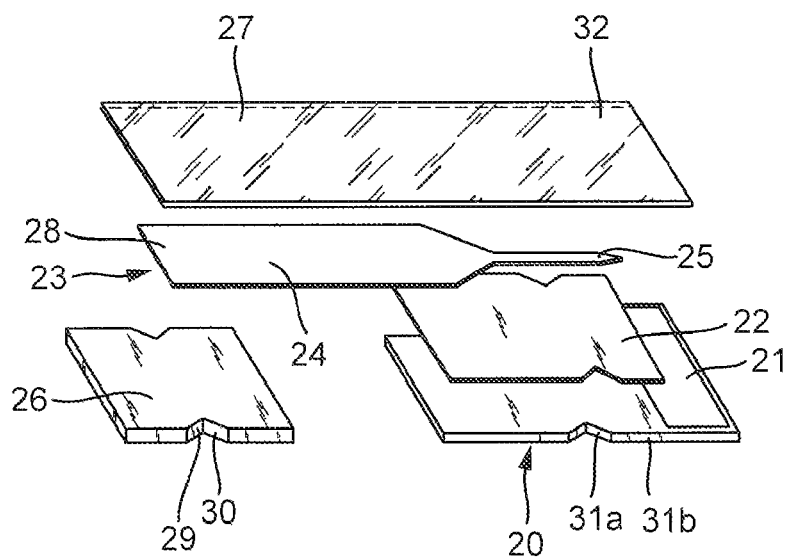

FIG. 3a shows an embodiment of a disposable 15 and FIG. 3b shows an exploded view of FIG. 3a. The disposable 15 can comprise an analyzing element 20 and a puncturing element 23. The analyzing element 20 can have a test field zone 21 and a spacer element 22 on one of its top sides 21a, the spacer element 22 being located behind the test field zone 21 in the puncturing direction. In one embodiment, the spacer element 22 can be glued onto the top side 21a. However, others suitable methods of attachment may be used. The spacer element 22 can be used as a spacer between the puncturing element 23 and the analyzing element 20, so that the puncturing element 23 does not contact the test field zone 21 on its puncturing path. The configuration of a disposable 15 having a spacer element 20 between an analyzing element and a puncturing element is described in detail in EP 07005222.0.

The puncturing element 23 can comprise a needle element 24 having a needle tip 25 and a carrier 26. The needle element 24 can have a capillary channel 24a, which can extend opposite to the puncturing direction from the needle tip 25. The capillary channel 24a can be located on the side facing toward the analyzing element 20 and can be a half-open groove, for example. The needle element 24 can completely be enclosed by a protective envelope 27. The protective envelope 27 can be glued to the needle element 24 on its rear end 28, diametrically opposite the needle tip 25. In the area of the needle tip 25, the protective envelope 27 can loosely enclose the needle tip 25, so that it can be movable in the protective envelope. The outside of the protective envelope 27 can also be glued onto the carrier 26 in the rear area 28 of the needle element 24. Thus, the carrier 26 and the needle element 24 can be coupled and connected to one another (via the protective envelope 27).

The carrier 26 can be formed by a film or a plastic part, whose thickness can be less than about 1 mm. For example, the carrier 26 can also contain the desiccant to keep dry the unused disposable 15 in the closed chamber 9. In one embodiment, the carrier 26 can have a coupling structure 29 on each of its lateral edges 26a on the minor sides 26b, which can extend in the puncturing direction. The coupling structure 29 can be a recess in the lateral delimitation profile of the carrier 26. The recess can also be an indentation, an undercut or a hole located in the boundary area in one of the flat sides of the carrier. The coupling structure 29 can also be formed by a pin or a projecting element. The coupling structure 29 can be coupled to a corresponding coupling element of the coupling unit 7 of the analysis instrument 2 in a formfitting way. Therefore, it is possible that a coupling structure 29 (e.g. a recess) can be located on only one minor side 26b.

In another embodiment, the coupling structure 29 can be located directly at the needle element 24 of the puncturing element 23 if no carrier 26 is used. Formfitting coupling between the coupling structure 29 in the needle element 24 and a coupling element of the coupling unit can take place through the (thin) protective envelope 27, in other words with the protective envelope 27 in between.

The analyzing element 20 can also have a coupling structure 31, to which a further coupling element of the coupling unit 7 can couple, preferably in a formfitting way. The coupling structure 31 of the analyzing element 20 can be implemented on the boundary area 20a. The coupling structure 31 can be a recess (shown), a pin, a hook, a hole, an oblong hole, or any similar feature. The coupling structure 31 can comprise a coupling structure 31a on the analyzing element 20 and a corresponding coupling structure 31b on the connected spacer element 22 of the analyzing element 20. The coupling structures 29,31 can be in the same plane and can be accessible from the same direction.

During the puncturing movement, the puncturing element 23 can be moved relative to the analyzing element 20, i.e., the carrier 26 being moved up to the analyzing element 20. The protective envelope 27, which can be connected in its front area 32 to the analyzing element 20 and/or the spacer element 22 and at its rear end 28 to the needle element 24, can be telescoped during the puncture movement of the puncturing element 23 like an accordion. This can cause the needle tip 25 to penetrate and exit the protective envelope 27.

In one embodiment, the coupling structures 29 and 31 can each be located on the same spatial direction of the disposable 15, so that coupling to a coupling unit can take place from the same direction. The two coupling structures 29 and 31 can thus be located in such a manner that, if the disposable 15 is stored in the magazine 3, a coupling unit can couple in each case from above through the top side 16 of the magazine 3. The coupling movement (for coupling the coupling unit to the coupling structures 29,31) can be a motion transversal to the puncturing movement and can take place in the same plane as the puncturing movement.

The disposable 15 can have the advantage that during its production, the needle element 24 of the puncturing element 23 can be hermetically enclosed by the protective envelope 27. Subsequently, the needle element 24 can be sterilized, for example, by gamma or electron beams. In a next step, the analyzing element 20 can be glued jointly with the spacer element 22 to the protective envelope 27. The carrier 26 can also be connected to the protective envelope 27. Alternatively, the carrier 26 can also be mounted even before the sterilization of the puncturing element 23.

FIGS. 4a-e show the magazine 3 and a part of the coupling unit 7 during different movement phases of the disposable 15. The coupling unit 7 can comprise a coupling element 33 for coupling to the coupling structure 29 of the puncturing element 23. The coupling element 33 can be located on an extension arm 34. A further coupling element 35 for coupling to the coupling structure 31 of the analyzing element 20 can also be located on the extension arm 34. The two coupling elements 33, 35 can be moved synchronously, or individually, relative to one another. Therefore, the puncturing element 23 and the analyzing element 20 can also be moved synchronously, or individually, relative to another. In one exemplary embodiment, the coupling elements 33, 35 can be pins which can ensure formfitting coupling to the coupling structure 29 and 31, respectively.

Figure 4A:
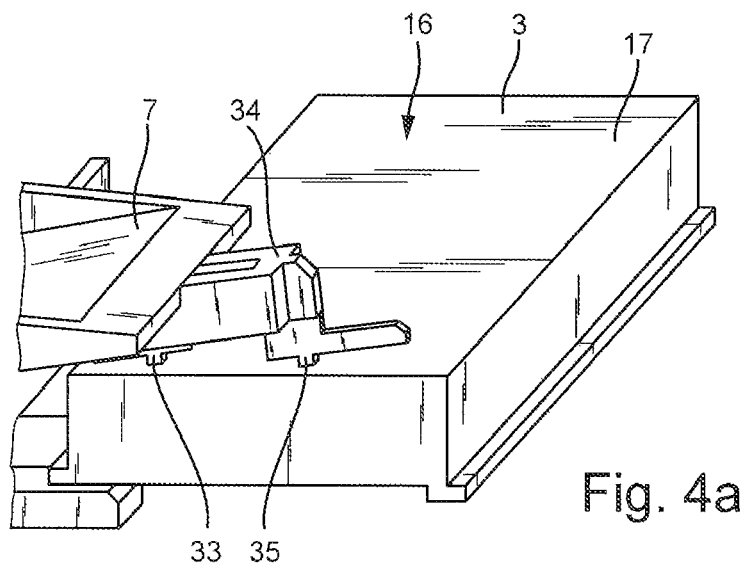
FIGS. 4a-e illustrate a detail view of the analysis system during the puncture procedure in different movement phases according to an embodiment of the present disclosure.
Figure 4B:
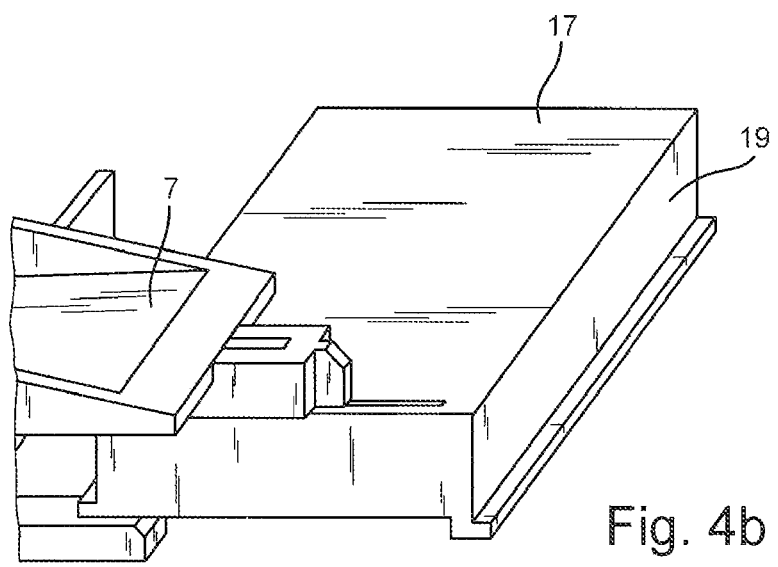

FIG. 4b shows how as the extension arm 34 of the coupling unit 7 is lowered (in direction to the magazine 3), the coupling elements 33 and 35 can penetrated the protective film 17. The film 17 can only be penetrated and destroyed in the area which covers the chamber 9 where the disposable 15 to be used is stored. The coupling elements 33 and 35 can be coupled in a formfitting way to the coupling structures 29 and 31, respectively. As the extension arm 34 of the coupling unit 7 moves in the puncturing direction, the two coupling elements 33 and 35 can moved synchronously to each another.

Figure 4C:
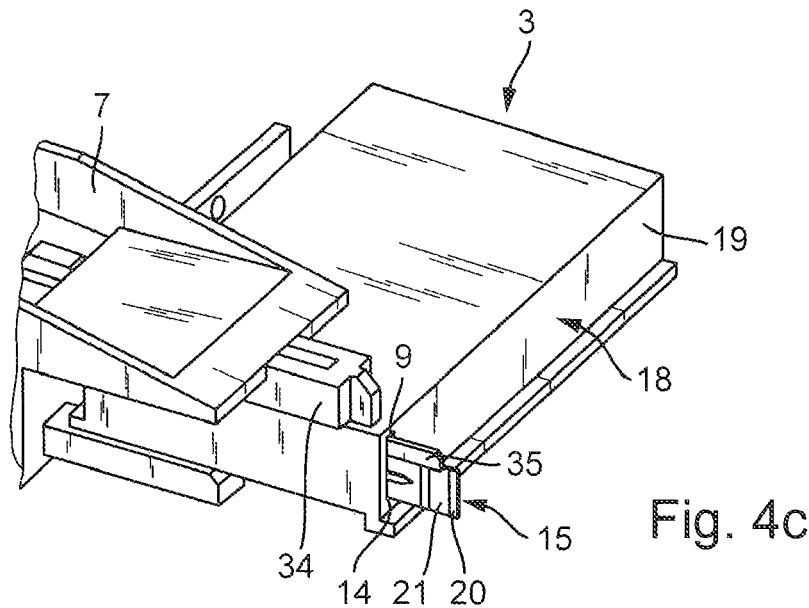

FIG. 4c shows the coupling elements 33, 35 of the extension arm 34 moved in the puncturing direction until the disposable 15 has penetrated the protective film 19 on the front side 18 of the magazine 3. The disposable 15 can be moved so far into the puncturing direction that the test field zone 21 of the analyzing element 20 can be located in front of an optical measuring apparatus of the measurement and evaluation unit 8. Alternatively, a relative movement of the two coupling elements 33, 35 to one another can be performed in such a manner that the needle tip 25 of the puncturing element 23 can project beyond the analyzing element 20 and the needle tip 25 can penetrate the protective film 19.

FIG. 4c shows the disposable 15 in its working position, in which the disposable 15 can project partially through the exit opening 14 and the test field zone 21 of the disposable 15 can be located outside the magazine 3. Because a large part of the disposable 15 remains in the chamber 9 of the magazine 3, good guiding by the chamber 9 of the magazine 3 during the puncture movement and in the working position can be ensured. It can be sufficient for the coupling elements 33, 35 to engage from above (i.e., from the top side 16 of the magazine 3) into the coupling structures 29, 31. Forces in and opposite to the puncturing direction can primarily be transmitted, but typically no transverse forces. The coupling elements 33, 35 can be very narrow and the disposable 15 can be very flat. In this way, many disposables 15 can be stored in the magazine 3 in a small space, which finally can result in a small overall size of the analysis instrument 2.

Figure 4D:
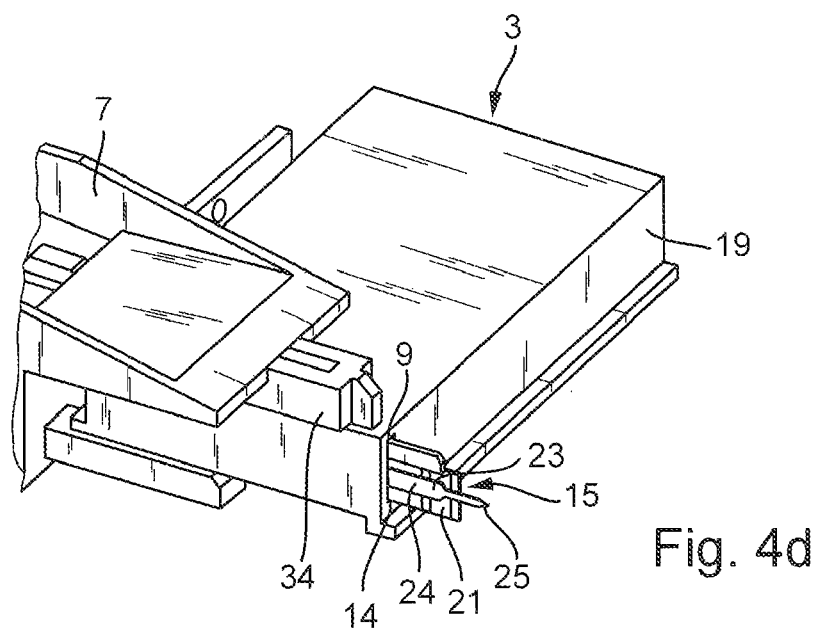

In FIG. 4d, the puncturing element 23 has executed a movement in relation to the analyzing element 20, so that the needle tip 25 projects beyond the analyzing element 20. In this position, a body part can be pierced to generate a wound. While the needle tip 25 is located in the body part, blood can be received in the capillary channel of the needle element 24. The capillary channel can be an open groove that can be hydrophilic, so that blood can be suctioned into the channel. Details of a puncturing element having a capillary channel are described extensively in the application EP 07005222 which has been incorporated by reference herein.

After the puncturing, the puncturing element 23 can be moved opposite to the puncturing direction by the coupling element 33 until the puncturing element 23 is located in a transfer position in relation to the analyzing element 20. In the transfer position, the sample outlet of the capillary channel can neighbor the test field zone 21. The transfer position can thus be a relative position of the puncturing element 23 to the analyzing element 20; the operational position, in contrast, can be the relative position of the analyzing element 20 to the magazine 3 and/or to the chamber 9.

Figure 4E:
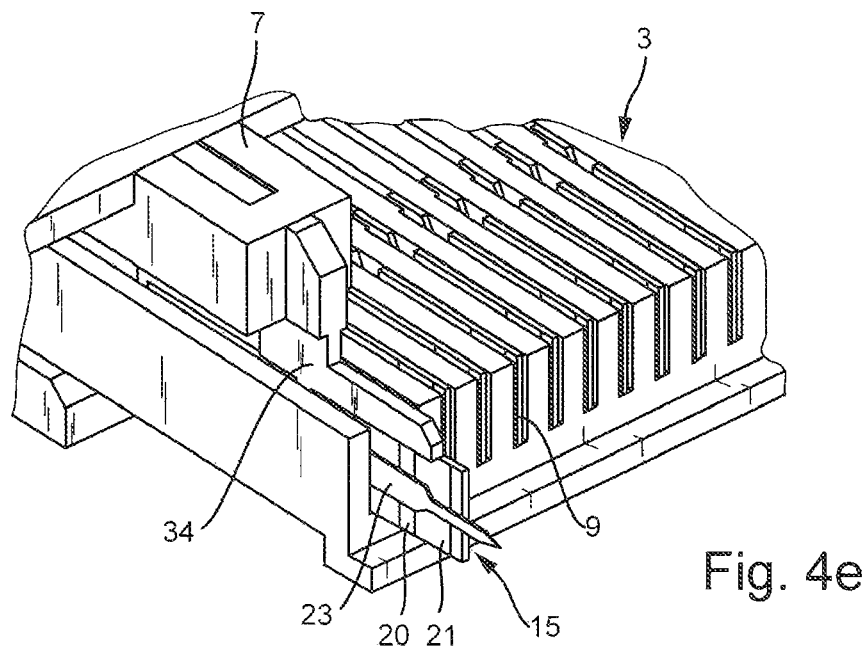

FIG. 4e shows the magazine 3 (without protective film 17, 19) and the puncturing element 23 being in the transfer position. The body fluid can be transferred to the test field zone 21. The test field zone 21 can include a test field which can comprise at least one absorbent layer. The test field of the test field zone 21 can have a receptacle surface, which can be located on the top side of the analyzing element 21a facing toward the puncturing element 23. A detection surface 37 on the diametrically opposite bottom side of the analyzing element 20 can contain a reagent system, typically, comprising a plurality of components, whose reaction to the body fluid can result in an optically measurable change of the detection surface 37.

To improve the sample transfer from the puncturing element 23 onto the test field zone 21, the puncturing element 23 and the analyzing element 20 can be pressed against one another. This can be performed by a contact pressure unit, for example.

As shown in the FIGS. 4a-e, the unused disposable 15 is in a first position (unused position). In this position, the puncturing element 23 can have no contact to the analyzing element 20. On the movement path of the disposable 15 to generate a wound in a body part and to analyze a body fluid exiting from the wound, the disposable 15 can be in a second position, in which the puncturing element 23 and the analyzing element 20 can be in contact to another. In one embodiment, the disposable 15 can extend only partially out of the chamber 9, so that the rear end of the disposable 15 can be contained in the chamber during the whole puncturing procedure. This means that the analyzing element 20 and the puncturing element 23 can be guided by the chamber 9 during the puncturing procedure because both elements 20,23 can extend only partially out of the chamber. Thus, the movement of the puncturing element 23 can be very stable which can result in a painless puncture of the finger tip.

Figure 5:
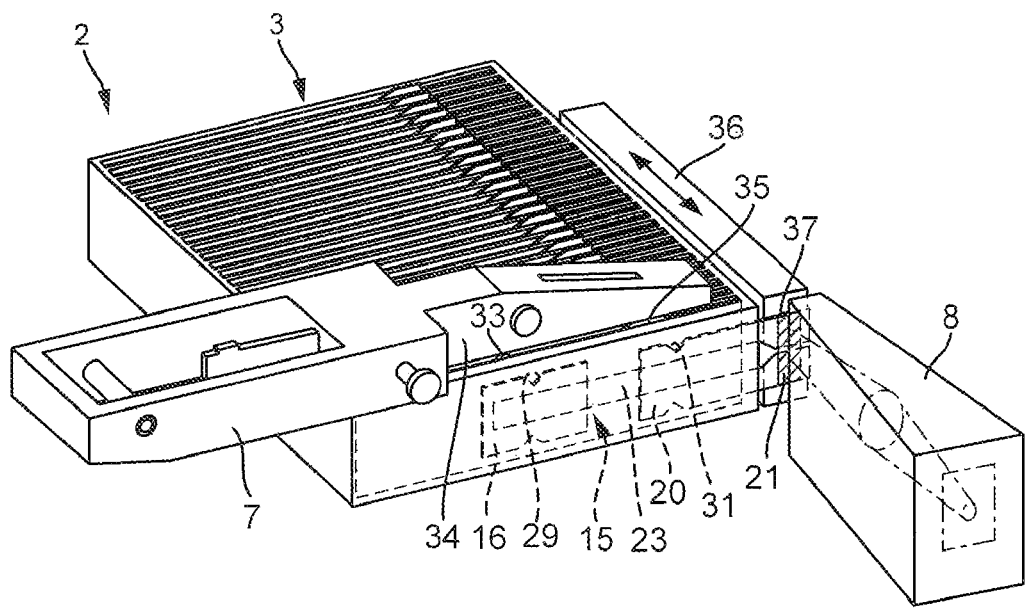
FIG. 5 illustrates a detail view of the analysis system during the determination of an analyte in a body fluid according to an embodiment of the present disclosure.

FIG. 5 shows a further detail view of the analysis instrument 2 according to the present invention having a magazine 3. Only the extension arm 34 and the two coupling elements 33, 35, which can engage in the corresponding coupling structures 29, 31 of the disposable 15, are shown of the coupling unit 7. The optical measuring and evaluation unit 8 can be located in front of the magazine 3 in the puncturing direction. The disposable 15 can be located in the operational position such that the test field zone 21 can be located outside the magazine 3. In the operational position, the test field zone 21 can be positioned in front of the optic of the optical measuring and evaluation unit 8.

The puncturing element 23 can be located behind the analyzing element 20 in the plane of the drawing. The measuring and evaluation unit 8 positioned transversely (e.g., perpendicular) to the puncturing direction can neighbor the bottom side of the analyzing element 20 and thus the detection surface 37, so that the distance between them may be only a few millimeters. A contact pressure unit 36, which can also be located in front of the magazine 3 in the puncturing direction, can press the puncturing element 23 against the analyzing element 20 to create contact between them and to improve the blood transfer. The contact pressure unit 36 can be a plunger, tappet, or the like, for example. During the contact pressure, the measurement and evaluation unit 8 can form a buttress to the contact pressure unit 36.

After the desired analyte has been determined in the blood, the disposable 15 can be moved back out of the operational position opposite to the puncturing direction until it is again completely positioned in the chamber 9. Preferably, the puncturing element 23 and the analyzing element 20 can be moved together, e.g., synchronically to another.

Then, the extension arm 34 of the coupling unit 7 can be moved upward, so that the coupling between the coupling elements 33, 35 and the coupling structures 29, 31 can be disengaged. The magazine 3 can be moved transversely to the puncturing direction, so that upon the next use of the analysis system 1, a sealed chamber 9 having an unused disposable 15 can be located below the coupling elements 33, 35 of the coupling unit 7. The system can then be ready for the next use.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analysis system for determining an analyte in a body fluid, the system comprising:
a magazine comprising a plurality of integrated sample acquisition and analyzing elements, each element comprises a puncturing element, an analyzing element and two major surfaces, the magazine comprising:
a plurality of elongate neighboring chambers separated by side walls running in a longitudinal direction of the plurality of elongate neighboring chambers having a height and length greater than their width, wherein the width is defined as the distance between two neighboring side walls, wherein the plurality of elongate neighboring chambers have two major sides delimited by the side walls and two long minor sides and two short minor sides extending between the side walls, wherein each chamber contains an integrated sample acquisition and analyzing element, wherein the puncturing element of the integrated sample acquisition and analyzing element has a coupling structure movable on a movement path of a puncture movement in a puncturing direction, and wherein each chamber has an exit opening on one of its minor sides for an at least partial exiting of the chamber by the puncturing element moving on the movement path; and a reusable analysis instrument, the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction,
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result;
a contact pressure unit located in front of the magazine in the puncture direction that is configured to apply force to a major surface of the puncturing element to bring the puncturing element into contact with the analyzing element;
a magazine holder for holding the magazine; and
wherein the plurality of elongate neighboring chambers are accessible by the coupling element on one of their long minor sides such that the coupling element can be formfitting coupled to the coupling structure of the puncturing element, when the puncturing element is positioned in the chamber and the magazine is located in the holder.

2. The analysis system according to claim 1, wherein the measuring and evaluation unit comprises an optical measuring apparatus for measuring an optically measurable measuring variable characteristic of the analyte.

3. The analysis system according to claim 1, wherein the magazine is advanced using the contact pressure unit.

4. The analysis system according to claim 1, wherein the plurality of elongate neighboring chambers are covered with a film on the long minor side on which the elongate neighboring chambers are accessible and/or on the short minor side in which the exit openings of the elongate neighboring chambers are located.

5. The analysis system or magazine according to claim 1, wherein the analyzing element of the integrated sample acquisition and analyzing element has a second coupling structure to which the coupling unit of the analysis instrument can be formfitting coupled.

6. The analysis system according to claim 5, wherein the coupling structure of the puncturing element and/or the second coupling structure of the analyzing element are located on an elongated minor side of the puncturing element and/or the analyzing element, respectively, such that the coupling unit of the analysis instrument can be formfitting coupled to the coupling structure and such that the puncturing element and the analyzing element are movable relative to another.

7. The analysis system according to claim 1, wherein,
the analyzing element has a test field zone,
the puncturing element has a capillary channel having at least one sample inlet and one sample outlet, and
the movement path of the puncturing element has a transfer position, in which the puncturing element is located relative to the analyzing element in such a position that the sample outlet of the capillary channel of the puncturing element neighbors the test field zone of the analyzing element so that a transfer of a body fluid from the capillary channel onto the test field zone can take place.

8. The analysis system according to claim 1, wherein the integrated sample acquisition and analyzing element is movable in the puncturing direction into an operational position such that the integrated sample acquisition and analyzing element at least partially extends out of the exit opening and that a test field zone of the analyzing element is positioned outside the chamber.

9. An analysis system for determining an analyte in a body fluid, the system comprising:
a magazine comprising a plurality of integrated sample acquisition and analyzing elements, each element comprises a puncturing element, an analyzing element and two major surfaces, the magazine comprising:
a plurality of elongate neighboring chambers separated by side walls running in a longitudinal direction of the plurality of elongate neighboring chambers having a height and length greater than their width, wherein the width is defined as the distance between two neighboring side walls, wherein the plurality of elongate neighboring chambers have two major sides delimited by the side walls and two long minor sides and two short minor sides extending between the side walls, wherein each chamber contains an integrated sample acquisition and analyzing element, wherein the puncturing element of the integrated sample acquisition and analyzing element has a coupling structure movable on a movement path of a puncture movement in a puncturing direction, and wherein each chamber has an exit opening on one of its minor sides for an at least partial exiting of the chamber by the puncturing element moving on the movement path; and
a reusable analysis instrument, the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction,
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result;
a magazine holder for holding the magazine;
wherein the plurality of elongate neighboring chambers are accessible by the coupling element on one of their long minor sides such that the coupling element can be formfitting coupled to the coupling structure of the puncturing element, when the puncturing element is positioned in the chamber and the magazine is located in the holder; and
wherein the analyzing element includes a test field zone and in an initial configuration of the integrated sample acquisition and analyzing element, the test field zone is positioned forward of a tip of the puncturing element in the puncturing direction and the integrated sample acquisition and analyzing element comprises a spacer element located between the analyzing element and the puncturing element such that the puncturing element on its movement path at least in the puncturing direction passes the test field zone of the analyzing element without contacting the test field zone.

10. An analysis system for determining an analyte in a body fluid, the system comprising:
a magazine comprising a plurality of integrated sample acquisition and analyzing elements, each element comprises a puncturing element, an analyzing element and two major surfaces, the magazine comprising:
a plurality of elongate neighboring chambers separated by side walls running in a longitudinal direction of the plurality of elongate neighboring chambers having a height and length greater than their width, wherein the width is defined as the distance between two neighboring side walls, wherein the plurality of elongate neighboring chambers have two major sides delimited by the side walls and two long minor sides and two short minor sides extending between the side walls, wherein each chamber contains an integrated sample acquisition and analyzing element, wherein the puncturing element of the integrated sample acquisition and analyzing element has a coupling structure movable on a movement path of a puncture movement in a puncturing direction, and wherein each chamber has an exit opening on one of its minor sides for an at least partial exiting of the chamber by the puncturing element moving on the movement path; and
a reusable analysis instrument, the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction,
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result;
a magazine holder for holding the magazine;
wherein the plurality of elongate neighboring chambers are accessible by the coupling element on one of their long minor sides such that the coupling element can be formfitting coupled to the coupling structure of the puncturing element, when the puncturing element is positioned in the chamber and the magazine is located in the holder; and
wherein the puncturing element is enclosed by a protective envelope, the protective envelope is connected to the puncturing element at a first location on the protective envelope and is connected to the analyzing element at a second location on the protective envelope and is telescoped upon a relative movement of the puncturing element relative to the analyzing element in the puncturing direction whereby the distance in the puncture direction between the first and second locations on the protective envelope is reduced, and wherein a tip of the puncturing element penetrates the protective envelope and extends out of the protective envelope.

11. An analysis system for determining an analyte in a body fluid, the system comprising a magazine and an analysis instrument;
the magazine comprising:
a plurality of flat, elongate, disposable integrated sample acquisition and analyzing elements, wherein each flat, elongate, disposable integrated sample acquisition and analyzing element comprises a puncturing element and an analyzing element and has two flat sides; and
a housing comprising a plurality of elongate neighboring chambers, wherein the plurality of elongate neighboring chambers are separated by two side walls running in a longitudinal direction of the plurality of elongate neighboring chambers having a height and length greater than the distance of two neighboring side walls, wherein the plurality of elongate neighboring chambers have two major sides delimited by the side walls and two long minor and two short minor sides extending between the side walls, wherein each chamber comprises an integrated sample acquisition and analyzing element, wherein the puncturing element of the integrated sample acquisition and analyzing element has a coupling structure movable on a movement path of a puncture movement in a puncturing direction, and wherein the analyzing element of the integrated sample acquisition and analyzing element has a second coupling structure, wherein each chamber has an exit opening on one of its minor sides for an at least partial exiting of the chamber by the puncturing element moving on the movement path, wherein the plurality of elongate neighboring chambers are accessible by the coupling element on one of their long minor sides such that the coupling element of a coupling unit of the analysis instrument can be formfitting coupled to the coupling structure of the puncturing element and that another coupling unit can be formfitting coupled to the coupling structure of the analyzing element, wherein the puncturing element and the analyzing element are movable relative to another such that the puncturing element is movable in a transfer position relative to the analyzing element to transfer body fluid;
the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction;
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result; and
a magazine holder for holding the magazine.

12. An analysis system for determining an analyte in a body fluid, the system comprising a magazine and an analysis instrument; the magazine comprising:
a plurality of flat, elongate, disposable integrated sample acquisition and analyzing elements, wherein the plurality of flat, elongate, disposable integrated sample acquisition and analyzing elements comprise a puncturing element and an analyzing element and having two flat sides, wherein
the magazine includes a plurality of neighboring chambers, each chamber contains an integrated sample acquisition and analyzing element, wherein the puncturing element of the integrated sample acquisition and analyzing element is enclosed by a protective envelope and is movable on a movement path of a puncture movement in a puncturing direction, each chamber has an exit opening allowing an at least partial exiting of the chamber by the integrated sample acquisition and analyzing element, and the plurality of neighboring chambers are covered with a film on at least one of their sides such that the plurality of neighboring chambers are completely closed;

the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction;
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result; and
a magazine holder for holding the magazine.

13. The analysis system according to claim 12, wherein the plurality of neighboring chambers, are elongated, are separated by two side walls running in a longitudinal direction of the plurality of neighboring chambers having a height and length greater than the distance of two neighboring side walls,
have two major sides delimited by the side walls and two long minor and two short minor sides extending between the side walls, wherein the exit opening is positioned on one of their minor sides, and
are covered with a film on the long minor side, on one of their minor sides, on the short minor side, on the major side, or combinations thereof.

14. The analysis system according to claim 13, wherein the film covering the plurality of neighboring chambers on their long minor side can be penetrated by a coupling element of a coupling unit of the analysis instrument.

15. The analysis system according to claim 12, wherein the puncturing element has a coupling structure, wherein the plurality of neighboring chambers are accessible on one of their long minor side such that a coupling element of a coupling unit of the analysis instrument can be formfitting coupled to the coupling structure of the puncturing element.

16. The analysis system according to claim 12, wherein the film for covering the minor sides of the plurality of neighboring chambers is at least partially metallic.

17. The analysis system according to claim 12, wherein the film covering the exit opening can be penetrated by the integrated sample acquisition and analyzing element and/or by the puncturing element on the movement path in the puncturing direction.

18. An analysis system for determining an analyte in a body fluid, the system comprising:
an analysis instrument; and
a magazine comprising a plurality of integrated sample acquisition and analyzing elements, each element having two flat sides and comprising an analyzing element and a puncturing element having a tip, wherein, the puncturing element is movable on a movement path of a puncture movement in the puncturing direction and in relation to the analyzing element, the puncturing element is enclosed by a protective envelope, the protective envelope is connected to the puncturing element at a first location on the protective envelope and is connected to the analyzing element at a second location on the protective envelope and is telescoped upon a relative movement of the puncturing element in relation to the analyzing element in the puncturing direction whereby the distance in the puncture direction between the first and second locations on the protective envelope is reduced, and wherein the tip of the puncturing element penetrates the protective envelope and extending out of the protective envelope;

the magazine having a plurality of elongate neighboring chambers separated by side walls running in a longitudinal direction of the plurality of elongate neighboring chambers having a height and length greater than their width, wherein the width is defined as the distance between two neighboring side walls, wherein the plurality of elongate neighboring chambers have two major sides delimited by the side walls and two long minor sides and two short minor sides extending between the side walls, wherein each chamber contains one of the plurality of integrated sample acquisition and analyzing elements; and the analysis instrument comprising:
a drive for driving the puncturing element in the movement path of the puncture movement, wherein the puncture movement includes a propulsion phase in the puncturing direction and, after reaching a reversal point, a retraction phase opposite to the puncturing direction;
a coupling unit coupling the integrated sample acquisition and analyzing element to the drive, wherein the coupling unit has a coupling element;
a measuring and evaluation unit for measuring a measurement variable characteristic of the analyte and for deriving therefrom a desired analysis result;
a contact pressure unit located in front of the magazine in the puncture direction that is configured to apply force to a major surface of the puncturing element to bring the puncturing element into contact with the analyzing element;
a magazine holder for holding the magazine; and
wherein the plurality of elongate neighboring chambers are accessible by the coupling element on one of their long minor sides such that the coupling element can be formfitting coupled to the coupling structure of the puncturing element, when the puncturing element is position in the chamber and the magazine is located in the holder.

19. The analysis system according to claim 18, wherein the puncturing element has a coupling structure to which a coupling unit of the analysis instrument can be coupled for moving the puncturing element on its movement path relative to the analyzing element.

20. Analysis system for determining an analyte in a body fluid, the system comprising:
a reusable analysis instrument; and
a magazine including a plurality of flat, disposable, integrated sample acquisition and analyzing elements, each comprising a puncturing element and an analyzing element and having two major surfaces;
the analysis instrument comprising:
a drive, by which a puncture movement of the puncturing element is driven, for movement on a movement path, the puncture movement including a propulsion phase in the puncturing direction and, after reaching a reversal point, a retraction phase opposite to the puncturing direction;

a coupling unit, adapted for coupling an integrated sample acquisition and analyzing element to the drive;

a measuring and evaluation unit for measuring a measurement variable characteristic for the determination of an analyte and for deriving therefrom a desired analysis result; and a magazine holder for holding the magazine;

the magazine comprising:

a plurality of elongate chambers located neighboring one another, the chambers being separated by side walls running in the longitudinal direction of the chambers, and having a height and length greater than its width, which is defined by the distance of two neighboring side walls; and wherein the chambers have two major sides delimited by the side walls and two long and two short minor sides extending between the side walls;

the chambers contain an integrated sample acquisition and analyzing element, whose puncturing element has a coupling structure and is movable on the movement path of the puncture movement in the puncturing direction, and whose analyzing element has a second coupling structure;

the chambers have an exit opening on one of their minor sides for allowing at least partial exiting out of the chamber of a puncturing element moved on the movement path;

the coupling unit has a coupling element and another coupling element;

the chambers of the magazine are accessible for the coupling element on one of their long minor sides such that the coupling element can be coupled to the coupling structure of the puncturing element and that the another coupling element can be coupled to the coupling structure of the analyzing element when the puncturing element and the analyzing element are positioned in the chamber of the magazine and the magazine is located in the holder.

* * * * *